United States Patent [19]

Kessel et al.

[11] Patent Number: 5,086,192

[45] Date of Patent: Feb. 4, 1992

[54] PHOTOPOLYMERIZABLE COMPOSITIONS AND PHOTOINITIATORS THEREFOR

[75] Inventors: Carl R. Kessel, St. Paul; Tracy R. Woodward, Cottage Grove, both of Minn.

[73] Assignee: Minnesota Mining and Manufacturing Company, St. Paul, Minn.

[21] Appl. No.: 627,498

[22] Filed: Dec. 14, 1990

[51] Int. Cl.$^5$ .................... C07F 7/18; C07F 13/00; C08F 22/250; C08G 59/30

[52] U.S. Cl. .................... 556/9; 428/413; 522/31; 522/170; 528/30; 556/12; 556/402; 556/423; 556/425; 556/428; 556/436; 556/446

[58] Field of Search ............. 556/9, 12, 402, 405, 556/423, 425, 428, 436, 446; 522/31

[56] References Cited

U.S. PATENT DOCUMENTS 4,005,024 1/1977 Rodriguez .................. 556/405
4,005,119 1/1977 Heckert ....................... 556/405
4,086,091 4/1978 Cella ........................... 556/402
4,116,886 9/1978 Cella ........................... 556/405

OTHER PUBLICATIONS

Chemical Abstract, vol. 110, No. 11, p. 645, Abstract No. 110:94585j, Mar. 13, 1989.

*Primary Examiner*—Marion E. McCamish
*Assistant Examiner*—Arthur H. Koeckert
*Attorney, Agent, or Firm*—Gary L. Griswold; Walter N. Kirn; Gregory A. Evearitt

[57] ABSTRACT

Disclosed are siloxanyl-substituted diaromatic iodonium salts such as 4-[3-1,1,3,3,5,5,5-heptamethyl siloxanyl propoxy]phenyl-phenyliodonium hexafluoroantimonate. These diaryl iodonium salts are useful as photoinitiators for epoxy containing compounds, especially epoxypolysiloxanes. Also disclosed is a process for the preparation of a siloxanyl-substituted diaromatic iodonium salt.

7 Claims, No Drawings

PHOTOPOLYMERIZABLE COMPOSITIONS AND PHOTOINITIATORS THEREFOR

FIELD OF THE INVENTION

This invention relates to aromatic iodonium salts. Furthermore, this invention relates to photopolymerizable compositions, and more particularly, it relates to such compositions which contain an aromatic iodonium salt as a photoinitiator.

BACKGROUND OF THE INVENTION

Photopolymerizable epoxy compositions containing epoxy resins and various photoinitiators are well known. However, because the existing systems all suffer from one or more drawbacks, there is a continuing need in the industry for improved photopolymerizable epoxy compositions. Thus, in U.S. Pat. No. 3,074,869, there are disclosed photosensitive epoxy compositions containing a nitrosoamine as a photoinitiator. Compositions of this type require relatively long exposure to a high intensity light source to produce complete polymerization.

In U.S. Pat. Nos. 3,205,157 and 3,708,296, there are disclosed photosensitive epoxy compositions containing aryldiazonium salts of halogen-containing complex anions. Such compositions have limited usefulness because they have poor thermal stability, because their spectral response is limited to the ultraviolet region of the spectrum, and because nitrogen is evolved during photopolymerization causing pinholes and bubbles in heavy coatings of the composition.

When these known aryldiazonium salts are used to induce polymerization of oxetanes, or mixtures of oxetanes with epoxy resins, e.g., as described in U.S. Pat. No. 3,835,003, the same types of problems are encountered. Although several patents describe various techniques for stabilizing mixtures of diazonium salts and epoxides, such techniques are not satisfactory for several reasons. For example, the increase in stability which is obtained is measured only in days. Also, the addition of stabilizers contaminates the compositions with nonreactive material which softens the resulting product and also reduces the rate of photocure. See, e.g., U.S. Pat. Nos. 3,711,390; 3,711,931; 3,816,278; 3,816,280; 3,816,281; and 3,817,845.

Various types of aromatic halonium (typically iodonium or sulfonium) salts have been proposed for use as photoinitiators in photopolymerizable epoxy compositions which do not have the drawbacks associated with nitrosoamine and aromatic diazonium salts.

For example, photopolymerizable epoxy compositions which comprise an epoxy-containing material and a photosensitive aromatic iodonium salt are described in U.S. Pat. No. 4,378,277. The aromatic groups of the iodonium salt may be substituted by one or more organic groups including alkoxy groups (e.g., methoxy, ethoxy, butoxy, and the like).

Reference to radiation curable compositions of an epoxy resin and an aromatic halonium salt is made in U.S. Pat. No. 3,968,056 and further discussed in U.S. Pat. No. 4,026,705 where it is disclosed that the aromatic group of the aromatic halonium salt can be substituted with from 1 to 4 monovalent radicals selected from groups including $C_1$ to $C_8$ alkoxy groups.

U.S. Pat. No. 4,101,513 discloses polymerizable compositions of a silane and an aromatic onium salt wherein the silane can be a hydrolyzable epoxy-terminated silane and the onium salt can be a diphenyliodonium salt.

U.S. Pat. No. 4,279,717 discloses epoxy functional diorganosiloxane fluids combined with bisaryl iodonium salts, particularly linear alkylate bisdodecylphenyl iodonium salts, that will rapidly dissolve in polysiloxane base polymer fluids.

U.S. Pat. No. 4,310,469 discloses as photoinitiators the diaryl iodonium salts of the formula:

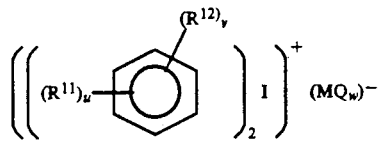

where:
M is a metal or metalloid;
Q is a halogen radical;
$R^{11}$ is a $C_{(4-20)}$ radical selected from alkyl, haloalkyl and branched alkyl;
$R^{12}$ is selected from $C_{(13)}$ alkyl, $C_{(18)}$ alkoxy, nitro and halo;
u is an integer having a value of from 1-4, inclusive;
v is a whole number having a value of 0-3, inclusive; and
w is an integer having a value of from 4-6, inclusive, and the sum of u and v has a value of from 1-4, inclusive.

Whereas the foregoing disclosed aromatic iodonium salts are all adequate for their intended use, improvements in the solubilities of aryl iodonium salts in photopolymerizable epoxy compositions, especially epoxypolysiloxanes, is continually sought by the industry. Increased solubility of the particular photosensitive compound in the photopolymerizable polymer solution will, of course, enhance photocuring of the polymer. This improves the performance of the photopolymerized polymer, such as, for example, when it is employed as a release coating for a pressure sensitive adhesive.

It was against this background that an improved photopolymerizable epoxy composition was sought.

SUMMARY OF THE INVENTION

By this invention, Applicants have discovered certain novel types of diaromatic iodonium salts which have enhanced solubilities in cationically photopolymerizable compositions and thus, make excellent photoinitiators therefor.

Thus, in one embodiment of the present invention are provided novel diaromatic iodonium salts wherein one of the aryl groups of the iodonium cation is substituted with a siloxanyl group, (—Si—O—Si—), and the anion of the salt is a halogen-containing complex anion.

Provided in another embodiment are photopolymerizable compositions which comprise: (a) a compound having a cationically polymerizable functionality; and (b) a siloxanyl group-substituted diaromatic iodonium salt. Preferably, the cationically polymerizable functionality is a vinyl ether or an epoxy containing compound and most preferably is an epoxypolysiloxane.

Provided in still another embodiment is a process for the preparation of a siloxanyl group-substituted diaromatic iodonium reaction product comprising the steps of: (a) heating a mixture of an aromatic idoso salt and siloxanyl group-substituted aromatic compound at about 50° to 100° C. in a polar solvent; (b) neutralizing the acid liberated from the aromatic iodoso salt, and (c) isolating the siloxanyl group-substituted diaromatic iodonium reaction product.

The novel siloxanyl group-substituted diaromatic iodonium salts of this invention have not been disclosed by any of the foregoing cited art. Their existence resides in the discovery that the condensation of an aromatic iodoso salt with a siloxanyl group-substituted aromatic compound can be carried out in the absence of additional acid such as is used in the conventional process for condensing aromatic idoso salts with an aromatic compound. The use of such additional acid with siloxanyl group-substituted aromatic compounds results in the loss of silyl content from the starting siloxanyl group-substituted aromatic compound.

The same siloxanyl group-substituted diaromatic iodonium salts of this invention, which have not been disclosed by any of the foregoing cited art, have excellent solubilities in cationically polymerizable materials such as epoxypolysiloxanes. They make excellent photoinitiators and enhance the performance properties of the photocured polymer.

Other aspects and advantages of the present invention will be apparent from the detailed disclosure, the examples, and the claims.

DETAILED DESCRIPTION OF THE INVENTION

The siloxanyl group-substituted aromatic iodonium salts of the present invention comprise: (a) a diaromatic iodonium cation wherein one of the aromatic groups is substituted with a siloxanyl group and (b) a halogen-containing complex anion.

Preferably, the diaromatic iodonium salts of the invention have the following formula:

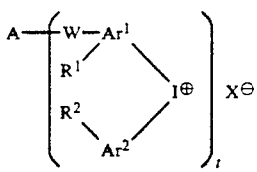

wherein:
- $Ar^1$ and $Ar^2$ are each independently aromatic having from 4 to 20 carbon atoms; preferably $Ar^1$ and $Ar^2$ are each independently selected from the group consisting of phenyl, thienyl, furanyl and pyrazolyl; and most preferably $Ar^1$ and $Ar^2$ are each phenyl;
- A is a mono- or polyvalent siloxanyl group having a valence of t and is represented by the formula:

$$-Si_nO_{n-1}R_{2n+2-t}$$

wherein t is a number having a value of about 1 to 10; and preferably is an integer having a value of 1 to 3; and n is a number having a value from 2 to about 150, preferably having a value of 2 to 20, and most preferably having a value of 2 to 6 when t is one and preferably n is a number having a value from 2 to about 70, most preferably having a value of 2 to 20 when t is 2 or 3; and R is an organic group selected from the group consisting of alkyl groups having 1 to 4 carbon atoms, alkenyl groups having 2 to 4 carbon atoms, and phenyl; preferably R is methyl;

- W is a divalent connecting group selected from the group consisting of alkylene groups having 2 to 6 atoms, alkyleneoxy groups having 2 to 6 carbon atoms; and a coordinate bond;
- $R^1$ and $R^2$ are each independently hydrogen, halogen, alkyl of 1 to 6 carbon atoms, alkoxy of 1 to 6 carbon atoms, or $R^1$ and $R^2$ together can constitute a divalent group joining $Ar^1$ and $Ar^2$ selected from the group consisting of

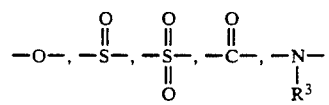

where $R^3$ is hydrogen or an alkyl group of 1 to 6 carbon atoms, a coordinate bond, or

where $R^4$ and $R^5$ are individually selected from hydrogen, an alkyl group of 1 to 4 carbon atoms, and an alkenyl group of 2 to 4 carbon atoms; preferably each of $R^1$ and $R^2$ is hydrogen; and

- X is a halogen-containing complex anion, and preferably is selected from the group consisting of tetrafluoroborate, hexafluorophosphate, hexafluoroarsenae, hexachlorantimonate, and hexafluorantimonate.

Preferably, the iodonium salts of the present invention are salts having a (siloxanyl group-substituted phenyl)phenyliodonium cation and a halogen-containing complex anion having the structural formula:

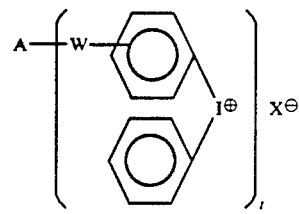

wherein A, W, t and X are as defined above.
The most preferred iodonium salts have the formulae:

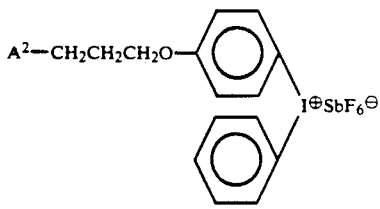

and

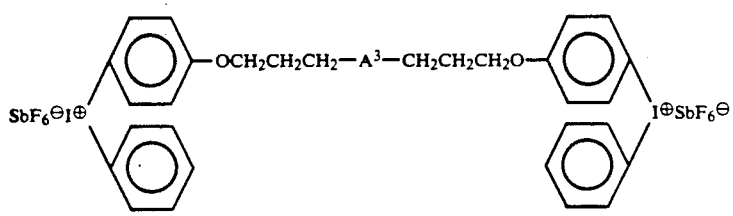

wherein $A^2$ is a monovalent siloxanyl group having the general formula:

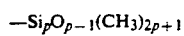

in which p is a number having the value from 2 to about 20 and preferably $a^2$ is selected from the group consisting of:

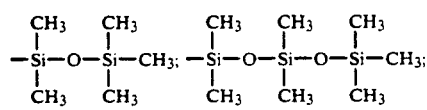

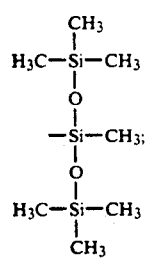

and

-continued

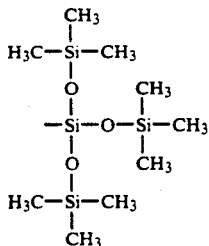

and $A^3$ is a siloxandiyl group having the general formula:

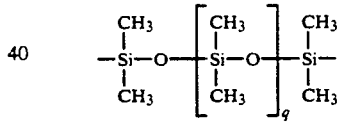

wherein q is a number having a value of zero to 70.

Non-limiting examples of the siloxanyl-substituted aromatic iodonium salts of the invention include:

Salt #1

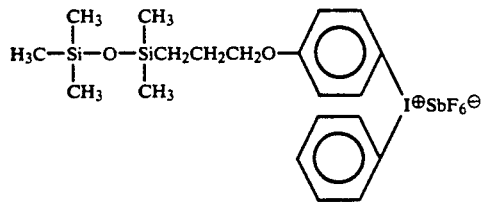

Salt #2

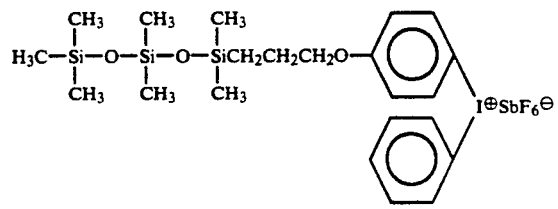

Salt #3

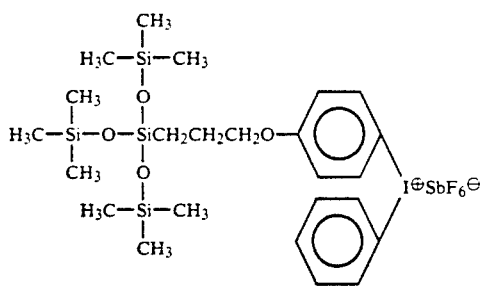
Salt #4
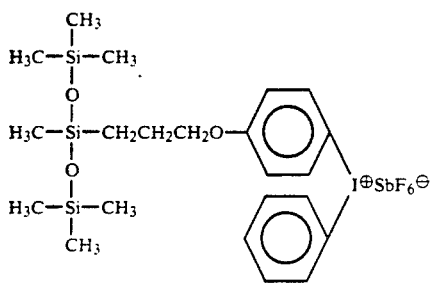
Salt #5
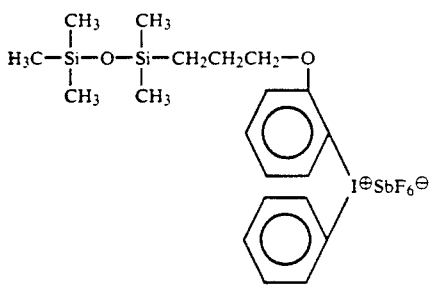
Salt #6
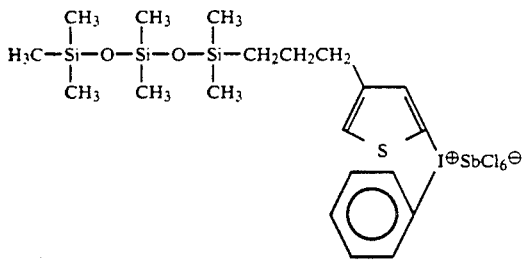
Salt #7
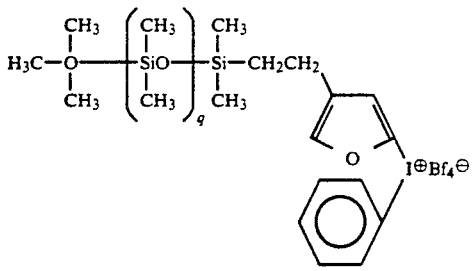
Salt #8

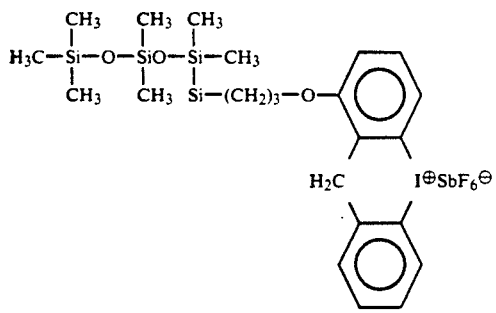
Salt #9
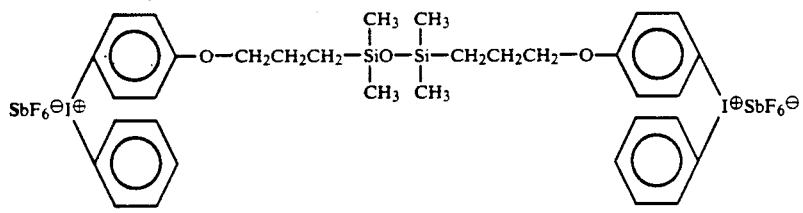
Salt #10
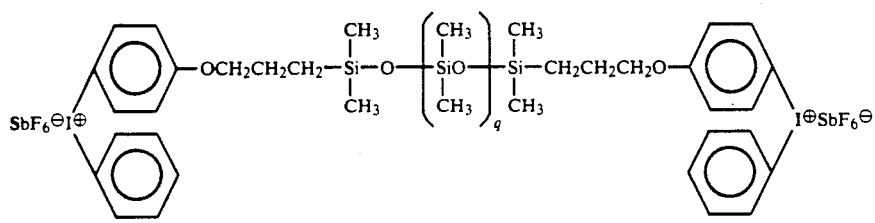
Salt #11
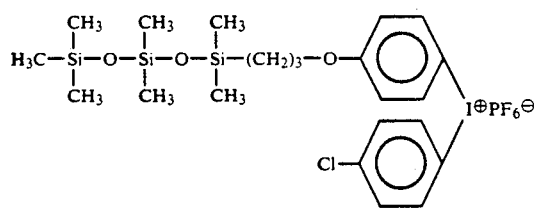
Salt #12
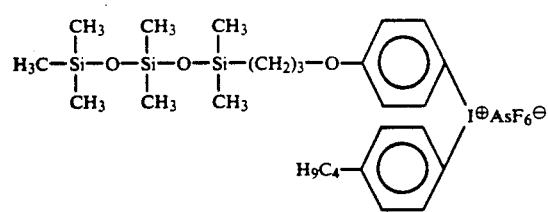
Salt #13
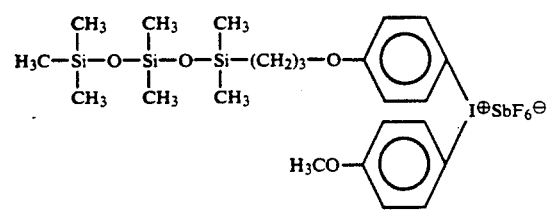
Salt #14

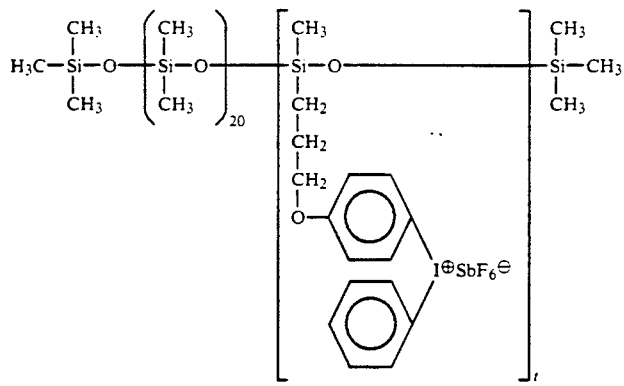

Aromatic iodonium salts are well known and recognized in the art. See, for example, U.S. Pat. Nos. 3,565,906; 3,712,920; 3,759,989, and 3,763,187; F. Beringer et al., Diaryliodonium Salts IX., J. Am. Chem. Soc. 81, 342-51 (1959); F. Beringer et al., Diaryliodonium Salts XXIII., J. Chem. Soc. 1964, 442-51; and F. Beringer et al., Iodonium Salts Containing heterocyclic Iodine, J. Org. Chem. 30, 1141-8 (1965).

Aromatic iodonium simple salts of the prior art may be prepared in accordance with Beringer et al., J. Am. Chem. Soc. 81, 342-51 (1959) by various methods including: (1) coupling of two aromatic compounds with iodyl sulfate in sulfuric acid; (2) coupling of two aromatic compounds with an iodate in acetic acid-acetic anhydride-sulfuric acid; (3) coupling of two aromatic compounds with an iodine acrylate in the presence of an acid; and (4) condensation of an iodoso compound, and aromatic iodoso diacetate, or an iodoxyl compound with another aromatic compound in the presence of an acid.

The siloxanyl group-substituted iodonium salts of the invention cannot be prepared as suggested by Beringer's method (4) above by the condensation of an aromatic iodoso compound, an aromatic iodoso diacetate, or an aromatic iodoxy compound with an siloxanyl group-substituted compound in the presence of an additional acid. In the absence of additional acid, the siloxanyl group-substituted iodonium can be prepared in accordance with the following schemes:

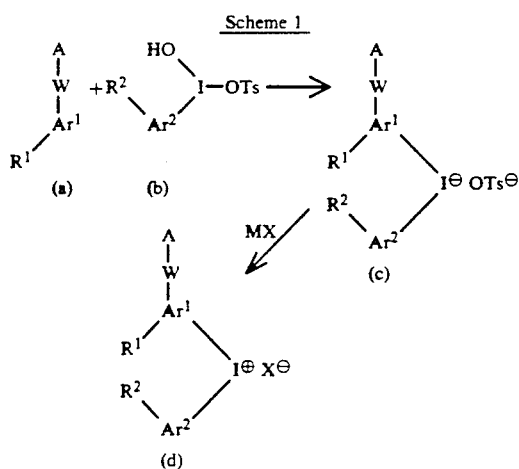

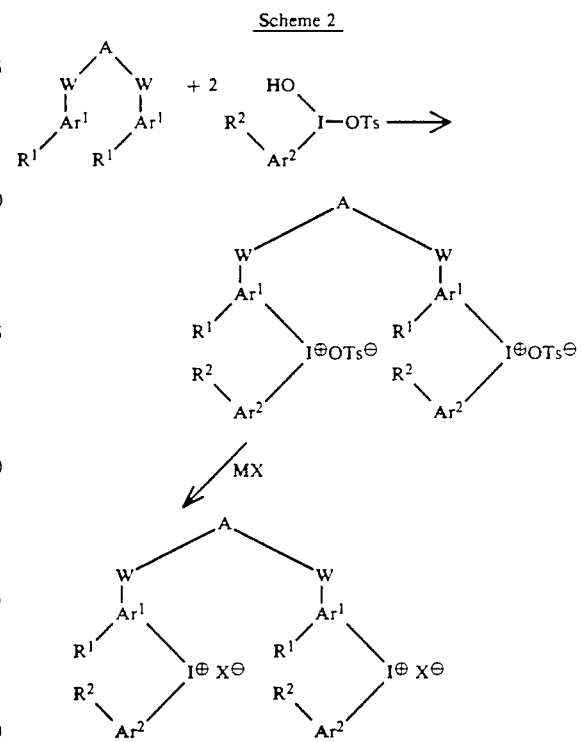

wherein $Ar^1$, $Ar^2$, $R^1$, $R^2$, A and W are defined earlier; and OTs is the tosylate group, i.e., p-toluenesulfonyl.

The siloxanyl group-substituted iodonium salts of the invention are prepared by a modification of the procedure given by Nieland and Karele, J. Org. Chem. USSR (Eng,) 6,889 (1970) for the preparation of phenyl (p-methoxyphenyl) iodonium tosylate by the condensation of an aromatic iodoso tosylate, (b), in the above scheme 1, with a siloxanyl group-substituted aromatic compound, (a) in the above scheme, without the addition of additional acid to the reaction mixture followed by a metathetical exchange of the tosylate anion by a halogen-containing complex anion. Thus, for example, the siloxanyl group-substituted diaromatic iodonium salts of Formula I:

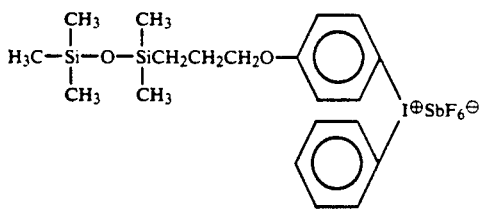

can be prepared by contacting at an elevated temperature, e.g., about 50° to 100° C., one equivalent by weight of phenyliodoso tosylate and one equivalent weight of 3-(pentamethyldisiloxanyl)propoxybenzene (prepared by the addition of pentamethyldisiloxane to allyloxybenzene in the presence of a platinum catalyst) in a polar aprotic solvent, e.g., acetonitrile for up to about one hour, preferably about 10 minutes, and then neutralizing the reaction mixture. The reaction product tosylate salt, (c) of Scheme 1, that is obtained does not need to be isolated but can be converted directly the hexafluorantimonate by metathesis with an alkali or alkaline earth metal salt of hexafluoroantimonic acid.

The polysiloxanes that are terminated by salt groups having a diaromatic cation and a halogen containing complex anion of Formula II, as for example,

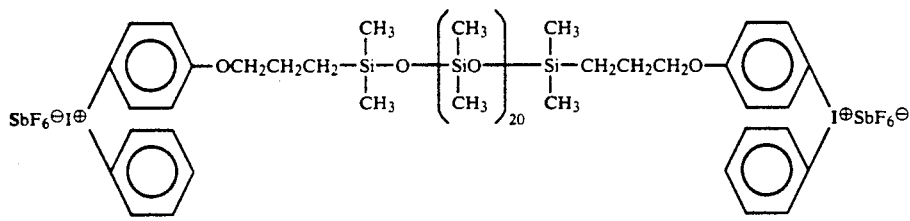

can be prepared in the manner of the above described preparation by heating at about 50° to 100° C. an equivalent weight of the phenoxypropyl-terminated polysiloxane;

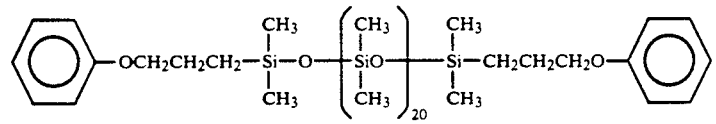

with two equivalent weights of phenyliodoso tosylate and converting the tosylate salt reaction product obtained to the desired hexafluoroantimonate salt by metathesis. The phenoxypropyl-terminated polysiloxane can be prepared by the hydrosilation of allylbenzene with a hydrogendimethylsiloxy terminated polydimethylsiloxane

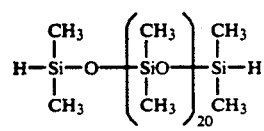

in the presence of a hydrosilation catalyst as is well known. The preparation of the hydrogendimethylsiloxy terminated polydimethylsiloxane is also well known and can be done by conventional acid catalyzed equilibration cohydrolysis of a mixture of hydrogendimethyl- silane, such as dimethyl chlorsilane, and 1,1,3,3-tetramethyldisiloxane.

Epoxy-containing compositions useful in the present invention are any organic compounds which have an oxirane ring polymerizable by ring opening. Such materials, broadly called epoxides, include monomeric epoxy compounds and epoxides of the polymeric type and can be aliphatic, cycloaliphatic, aromatic, or heterocyclic. These materials generally have at least one polymerizable epoxy group per molecule (preferably two or more epoxy groups per molecule) and in the polymeric type there may be many pendant epoxy groups (e.g., a glycidyl methacrylate polymer could have several thousand pendant epoxy groups per average molecular weight).

These epoxy-containing materials may vary from low molecular weight monomeric materials to high molecular weight polymers and may vary greatly in the nature of their backbone and substitutent groups. For example, the backbone may be of any type and substitutent groups thereon can be any group not having an active hydrogen atom which is reactive with an oxirane ring. Illustrative of permissible substitutent groups include halogens, ester groups, nitro groups, amide groups, nitrile groups, phosphate groups, etc. The molecular weight of the epoxy-containing materials may run up to 100,000 or more.

Mixtures of various epoxy-containing materials can also be used in the compositions of this invention. Such epoxy-containing materials are well known and include such epoxides as epichlorohydrins, e.g., epichlorohydrin; alkylene oxides, e.g., propylene oxide, styrene oxide; alkenyl oxides, e.g., butadiene oxide; glycidyl esters, e.g., ethyl glycidate; glycidyl-type epoxy resins, e.g., the diglycidyl ethers of Bisphenol A and of novalak resins, such as described in the "Handbook of Epoxy Resins" by Lee and Neville, McGraw-Hill Book Co., New York (1967).

Other useful epoxy-containing materials which can be used in this invention are those which contain one or more cyclohexene oxide groups. (In Chemical Abstracts, the term used is 7-oxabicyclo[4.1.0]heptane) such as epoxycyclohexanecarboxylates, typified by 3,4-epoxycylcohexylmethyl 3,4-epoxycyclohexanecarboxylate, 3,4-epoxy-2-methylcyclohexylmethyl 3,4-epoxy-2-methylcyclohexanecarboxylate, and bis(3,4-epoxy-6-methylcyclohexylmethyl) adipate. For a more detailed list of useful epoxides of this nature, see, U.S. Pat. No. 3,117,099.

Further epoxy-containing materials which are particularly useful in the practice of this invention include glycidyl ether monomers of the formula:

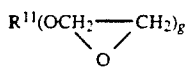

where $R^{11}$ is alkyl or aryl and g is an integer of 1 to 6. Examples are the glycidyl ethers of polyhydric phenols obtained by reacting a polyhydric phenol with an excess of a chlorohydrin such as epichlorohydrin (e.g., the diglycidyl ether of 2,2-bis(2,3-epoxy propoxyphenyl)-propane). Further examples of epoxides of this type which can be used in the practice of this invention are described in U.S. Pat. No. 3,018,262.

The epoxypolysiloxanes particularly suitable for use in the compositions of this invention, in which the siloxanyl group-substituted salts have improved solubility, are represented by the formula:

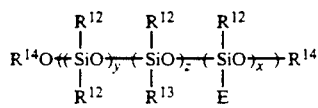

wherein:

$R^{12}$ is a lower alkyl group of one to three carbon atoms;

$R^{13}$ is a monovalent hydrocarbyl group of 4 to 20 carbon atoms; and preferably, an alkyl group of 4 to 8 carbon atoms, phenyl, or 2-phenylethyl;

$R^{14}$ is $R^{12}{}_3Si-$, $R^{12}{}_2ESi-$, or $R^{12}{}_2R^{13}Si-$;

E is an oxiranyl group-substituted monovalent linear, branched, or cyclic aliphatic group having 2 to 300 or more carbon atoms and optionally, up to 100 or more non-peroxidic oxygen atoms; and q is a number having a value of about 1 to about 75 with the proviso that when x is zero then $R^{14}$ is $R^{12}ESi-$; and x, y and z are independently zero or a number having a value up to 200, preferably x is a number having a value between 3 and 50 and y is a number having a value between 33 and 150 such that, when considered with the value of q, the epoxypolysiloxane has a number average molecular weight between 500 and 100,000, preferably between 2,000 and 15,000 and a viscosity of about 100 to 25,000 centistokes.

Illustrative examples of the monovalent organic group $R^{12}$ in the above formula are alkyl groups such as methyl, ethyl, and propyl. Examples of the monovalent organic groups $R^{13}$ are butyl, isobutyl, tertbutyl, hexyl, octyl and octadecyl; aryl groups, such as phenyl, tolyl and xylyl; aralkyl groups such as phenylmethyl, phenylethyl, phenylpropyl and phenylhexyl; cycloaliphatic groups such as cyclopentyl, cyclohexyl and 3-cyclohexylpropyl; and ether oxygen—or ester oxygen-containing groups such as ethoxypropyl, butoxybutyl, and ethoxycarbonylpropyl and the like.

The most preferred $R^{12}$ group is methyl and the most preferred $R^{13}$ group is phenyl. The siloxane groups in the above formula for the epoxypolysiloxane can be randomly arranged where $R^{12}$ varies from one group to the next.

The monovalent epoxy group-substituted hydrocarboyl group, E, contains at least one polymerizable epoxy group,

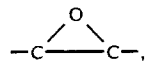

the remainder of the group being composed of carbon and hydrogen and free of acetylenic unsaturation. In addition to the oxirane oxygen, the group can contain ether oxygen, i.e., —O—; carbonyl oxygen, i.e.,

or ester groups, i.e.,

Illustrative examples of E groups are:

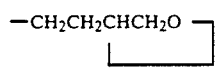

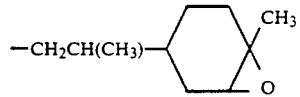

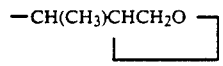

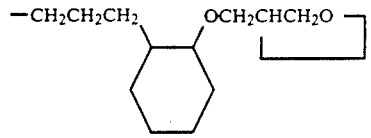

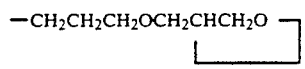

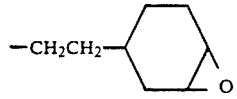

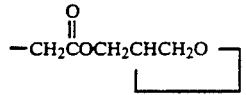

In the above epoxy group-containing aliphatic groups, the epoxy group is preferably located at the terminal position of the group.

Due to the availability of starting materials and the ease of preparation and performance, the preferred epoxypolysiloxanes are those whose $R^{12}$ is methyl and E is beta-(3,4-epoxycyclohexyl)ethyl or gamma-glycidoxypropyl.

The epoxypolysiloxanes can be prepared by many methods known in the art such as the chloroplatinic acid catalyzed addition reaction of hydrosiloxanes containing the —SiH reactive group with aliphatically unsaturated epoxy compounds; epoxidation of vinyl, alkenyl or other unsaturated siloxanes; and Grignard type reactions such as, for example, described by E. P. Pluedemann and G. Fanger, J. Am. Chem. Soc. 81, 2632–35 (1959). A convenient method is the hydrosiloxane addition reaction.

The photopolymerizable compositions of the present invention can be made by admixing the siloxanyl group-substituted aromatic iodonium salts and other photoinitiator when used, with the epoxy-containing organic material. The solventless compositions are prepared by dissolving the substituted aromatic iodonium salt and other photoinitiator in the organic material with or without the use of mild heating. The amount of siloxanyl group substituted aromatic iodonium salts employed in the present invention range from about 0.005 to 5 parts, and preferably about 0.5 to 2.0 parts, per 100 parts of cationically polymerizable material.

The siloxanyl group-substituted aromatic iodonium complex salts useful in the compositions of the invention are of themselves photosensitive to radiation only in the ultraviolet range of the spectrum. They, however, can be sensitized to radiation in the near ultraviolet and the visible range of the spectrum by sensitizers for known photolyzable organic halogen compounds in accordance with the teachings of U.S. Pat. No. 3,729,313. Illustrative sensitizers are found in the following categories: aromatic amines and colored aromatic polycyclic hydrocarbons. The use of strongly basic amino compounds is less desirable.

Wavelengths of radiation to which the polymerizable compositions of the invention are sensitive are in the 200 to 600 nm range, preferably 200 to 450 nm. Suitable sources include sunlight, carbon arcs, mercury vapor arcs, black light lamps, fluorescent lamps, argon and xenon glow lamps, electronic flash units and flood lamps. Depending on the concentration of the iodonium salt, the particular epoxypolysiloxane, and the depth of the composition, exposures necessary to polymerize (which term includes crosslink and cure) the composition range from about 1 second or less to about 10 minutes or longer. Where the activating radiation is above about 300 nm, it is desirable to include in the photosensitive radiation sensitizer such as 1,3-diphenylisobenzofuran, 2-isopropyl thioxanthone or 1,3-diphenyl-2-pyrazoline. Other useful sensitizers are disclosed in U.S. Pat. No. 4,250,053.

The polymerization of the composition of the invention is a triggered reaction, i.e., once the degradation of the aromatic iodonium complex salt has been initiated by exposure to a radiation source, the hardening reaction proceeds and will continue after the radiation source is removed. The use of thermal energy during or after exposure to a radiation source will generally accelerate the hardening reaction and even a moderate increase in temperature may greatly accelerate the hardening rate.

Substrates which may be coated with the polymerizable compositions of the present invention include substrates of wood, fiberboard, particle board, paper and cardboard; synthetic and natural polymers such as polyolefins, polyesters, cellulose esters, polyamides, cured phenolics, urea-formaldehyde resins, poly(vinyl halides), polyacrylates, polyurethanes, proteins, and rubber; inorganic substrates such as iron, stainless steel, copper, brass, bronze, aluminum, titanium, nickel, zinc and alloys. Particularly useful substrates are paper, silicated aluminum, polypropylene, poly(vinyl)chloride, the polyesters such as polyethylene terephthalate, and cellulose esters such as cellulose acetate.

The solventless actinic radiation polymerizable compositions of the invention are particularly suitable for preparing release liners for use with adhesive roll and sheet materials. For this use, a substrate of paper or a film of polymers such as, for example, polyester, polyamide, polyolefin, etc., is used. Where needed, primers such as 2-(3,4-epoxycyclohexyl)ethyltrimethoxysilane may be used to improve adherence of the radiation-cured composition to the substrate without effecting the release performance of the epoxypolysiloxane coating.

In the examples given later herein, evaluation of release coatings prepared using the aromatic iodonium salts of the present invention was done by the following tests:

Release Value

A standard pressure-sensitive adhesive tape having an acrylic pressure-sensitive adhesive, i.e., a 95.5:4.5 isooctyl acrylate:acrylate acid copolymer, as described in U.S. Pat. No. RE 24,906, was pressed against the surface of a release coated substrate using two passes of a 2 kg rubber roller to produce a laminate. The laminate was cut into $2.5 \times 25$ cm strips and attached, substrate side down, to a smooth stainless steel panel. The release value is the force, in grams, required to pull the pressure-sensitive adhesive tape with adhesive adhered thereto away from the release coated substrate at an angle of 180° and a pulling speed of 225 cm/min.

Heat Aged Release Value

A laminate of standard pressure-sensitive adhesive tape and release coated substrate was prepared as described above and heated in an oven at 70° C. for 72 hours. After this time, the laminate was removed from the oven, allowed to cool for at least 10 minutes in a room at $23° + 0.2°$ C. and $50 + 2\%$ R. H. and within 2 hours after removal from the oven, the force required to pull the pressure-sensitive tape with adhesive adhered thereto away from the release coated substrate was measured as described in the above test.

EXAMPLE 1

The following procedure describes the preparation of Salt #4 and presents a standard procedure for the preparation of any siloxanyl group-substituted aromatic iodonium salt.

Into a 5 liter 3-neck flask, fitted with mechanical stirrer, internal thermometer, and reflux condenser were placed 1,1,1,3,5,5,5-heptamethyl-3-(3-phenoxypropyl)trisiloxane (prepared hydrosilation of allyl phenyl ether with 1,1,1,3,5,5,5-heptamethyltrisiloxane) (495.5 gm, 1.389 moles) and acetonitrile (1478 gm.). The flask was heated until the internal temperature reached 80° C., and phenyliodoso tosylate (1089 gm., 2.78 moles) was added in one portion. The solution was allowed to stir at 80° C. for 8 minutes, after which solid NaHCO$_3$ (400 gm.) was added at such a rate as to keep the foaming under control (about 3 minutes). The bright yellow reaction was allowed to cool, filtered, and solvent was removed from the orange-yellow filtrate under reduced pressure. Final removal of solvent under high vacuum gave a sticky yellow solid (812 gm) which NMR spectroscopy showed to be 86% iodonium tosylate salt with the major impurity being iodobenzene (Y $0.86 \times 812 = 698$ gm., 0.956 mole, 69%).

The tosylate salt product (698 gm) was dissolved in methyl ethyl ketone (1036 gm) and a solution of NaSbF$_6$ (237.3 gm) in methyl ethyl ketone (500 gm) was added in one portion. A large amount of white precipitate formed immediately, and the reaction was allowed to stir at room temperature for one hour. The reaction was filtered and the clear red filtrate was stripped of volatiles under high vacuum to give a thick red syrup (718 gm) which NMR spectroscopy showed to be the desired product, Salt #4.

Two parts by weight of the above product Salt #4 was mixed into an epoxypolysiloxane of the following formula (98 parts by weight):

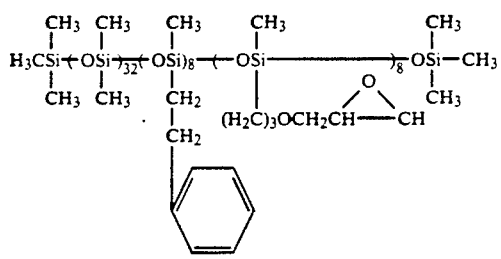

and a 1 micron thick layer of the resulting clear homogeneous mixture was coated onto biaxially-oriented polypropylene film (BOPP). The coated film was passed under 4 medium pressure mercury lamps to give a tack-and-smear-free coating which adhered well to the substrate. The release value of this coating was found to be 19 g/cm width. Aged release was 16 g/cm width.

EXAMPLE 2

A iodonium salt in which the siloxane substituent is at the terminus of the siloxane backbone was prepared using the same procedure as given in Example 1, except that 1,1,3,3,5,5,5-heptamethyl-1-(3-phenoxypropyl)-trisiloxane was used. The product of this reaction was a red syrup which NMR showed to be Salt #2 of about 85% purity.

A formulation of 2 parts of this material with 98 parts of the same epoxypolysiloxane used in Example 1 was prepared, and this mixture was also clear and homogeneous. This formulation was coated as a 1 micron layer on polyethylene coated kraft paper and cured under 4 medium pressure mercury lamps to give a tack-and smear-free coating which adhered well to the substrate. The release value of this coating was found to be 15 g/cm width. Aged release was 18 g/cm width.

EXAMPLE 3

A difunctional iodonium salt in which the siloxane substituent is a polydimethylsilxane chain bridging between the two iodonium salts was prepared using the same procedure as given in Example 1, except that a dimethyl-(3-phenoxypropyl)siloxy end-capped polydimethylsiloxane with an average chain length of 20 dimethylsiloxy units was used. The product of this reaction was red syrup which NMR showed to be Salt #10 in which n=20 and greater than 80% purity.

A formulation of 2 parts of this material with 98 parts of the same epoxypolysiloxane used in Example 1 was prepared. The solution obtained was clear and homogeneous. This formulation was coated as a 1 micron layer on a polyethylene coated Kraft paper and cured under 4 medium pressure mercury lamps to give a tack-and smear-free coating which adhered well to the substrate.

The release value of this coating was found to be 16 g/cm width. Aged release was 16 g/cm width.

Following the same procedure that was used in Example 1, there were prepared iodonium salts using in place of 1,1,1,3,5,5,5,-heptamethyl-3-(3-phenoxypropyl)trisiloxane the siloxanes 1,1,3,3,3-pentamethyl-1-(3-phenoxypropyl)disiloxane to prepare Salt #1; 1,1,1,-trimethyl-3,3-di(trimethylsiloxy)-3-(3-phenoxypropyl)-disiloxane to prepare Salt #3; and 3-phenoxypropyl end-capped polydimethylsiloxanes having average number of dimethylsiloxy units of 0, 40, 70, and 130 to prepare, respectively, #10 Salts in which n was 0, 40, 70, and 130.

Each of these salts are soluble in epoxypolysiloxane and can be coated onto substrates and radiation cured to provide tack- and smear-free coatings that adhere well to the substrate.

Reasonable modifications and variations are possible from the foregoing disclosure without departing from either the spirit or scope of the present invention.

What is claimed is:

1. A diaromatic iodonium salt comprising: (a) a diaromatic iodonium cation wherein one of the aromatic groups is substituted with a siloxanyl group; and (b) a halogen-containing complex anion.

2. A diaromatic iodonium salt according to claim 1 represented by the formula:

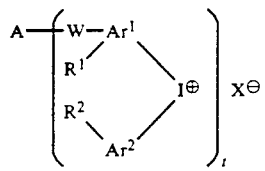

wherein:

Ar$^1$ and Ar$^2$ are each independently aromatic having from 4 to 20 carbon atoms;

A is a mono- or polyvalent siloxanyl group having a valence of t and is represented by the formula:

wherein t is a number having a value of about 1 to 10; n is a number having a value from 2 to about 150; R is an organic group selected from alkyl groups having 1 to 4 carbon atoms, alkenyl groups having 2 to 4 carbon atoms, and phenyl;

W is a divalent connecting group selected from the group consisting of alkylene groups having 2 to 6 atoms, alkylenoxy groups having 2 to 6 carbon atoms; and a coordinate bond;

R$^1$ and R$^2$ are each independently hydrogen, halogen, alkyl of 1 to 6 carbon atoms, alkoxy of 1 to 6 carbon atoms, or R$^1$ and R$^2$ can together constitute a divalent group joining Ar$^1$ and Ar$^2$ selected from the group consisting of

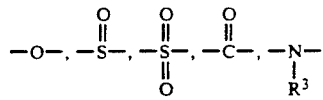

where R$^3$ is hydrogen or an alkyl group of 1 to 6 carbon atoms, a coordinate bond, or

where $R^4$ and $R^5$ are individually selected from hydrogen, an alkyl group of 1 to 4 carbon atoms, and an alkenyl group of 2 to 4 carbon atoms; and X is a halogen-containing complex anion.

3. A diaromatic iodonium salt according to claim 2 wherein $Ar^1$ and $Ar^2$ are independently selected from the group consisting of phenyl, thienyl, furanyl, and pyrazolyl.

4. A diaromatic iodonium salt according to claim 2 wherein $R^1$ and $R^2$ are hydrogen.

5. A diaromatic iodonium salt according to claim 2 wherein X is selected from the group consisting of tetrafluoroborate, hexafluorophosphate, hexafluoroarsenate, hexachloroantimonate, and hexafluoroantimonate.

6. A diaromatic iodonium salt according to claim 1 and selected from the group consisting of:

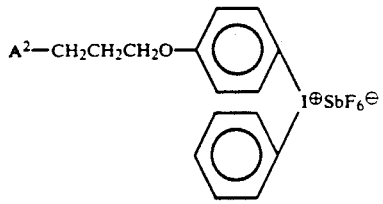

and

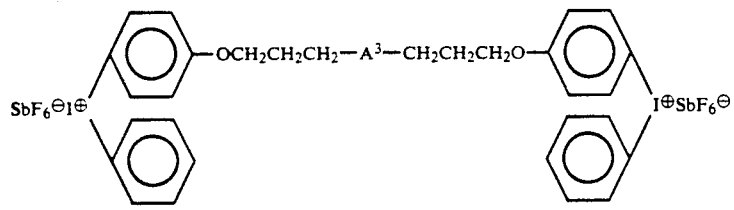

wherein $A^2$ is a monovalent siloxanyl group having the general formula:

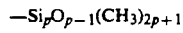

$A^3$ is a siloxandiyl group having the general formula:

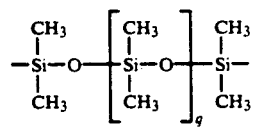

p is a number having a value from 2 to about 20 and q is a number having a value from zero to about 70.

7. A diaromatic iodonium salt according to claim 6 wherein $A^2$ is selected from the group consisting of:

$$-\underset{\underset{CH_3}{|}}{\overset{\overset{CH_3}{|}}{Si}}-O-\underset{\underset{CH_3}{|}}{\overset{\overset{CH_3}{|}}{Si}}-CH_3.$$

$$-\underset{\underset{CH_3}{|}}{\overset{\overset{CH_3}{|}}{Si}}-O-\underset{\underset{CH_3}{|}}{\overset{\overset{CH_3}{|}}{Si}}-O-\underset{\underset{CH_3}{|}}{\overset{\overset{CH_3}{|}}{Si}}-CH_3$$

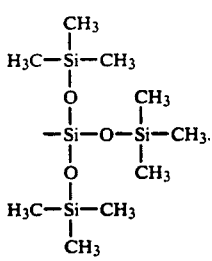

and $$H_3C-\underset{\underset{\underset{H_3C-\underset{\underset{CH_3}{|}}{\overset{\overset{O}{|}}{Si}}-CH_3}{|}}{\overset{\overset{O}{|}}{Si}}-O-\underset{\underset{CH_3}{|}}{\overset{\overset{CH_3}{|}}{Si}}-CH_3}{|}}{\overset{\overset{CH_3}{|}}{Si}}-CH_3.$$

* * * * *